United States Patent [19]

Rieu

[11] Patent Number: 5,071,850

[45] Date of Patent: Dec. 10, 1991

[54] 2,3-DIHYDRO-3-ARYLALKYLAMINOAL-KYL-4H-1,3-BENZOXAZIN-4-ONE DERIVATIVES, THEIR PREPARATION AND THEIR APPLICATION AS MEDICINAL PRODUCTS WHICH ARE USEFUL IN THERAPY

[75] Inventor: Jean-Pierre Rieu, Castres, France

[73] Assignee: Pierre Fabre Medicament, Paris, France

[21] Appl. No.: 403,757

[22] Filed: Sep. 6, 1989

[30] Foreign Application Priority Data

Sep. 8, 1988 [FR] France .................. 88 11746

[51] Int. Cl.⁵ .................. C07D 265/22; C07D 265/12; C07D 498/04; A61K 31/535
[52] U.S. Cl. .................. 514/229.8; 514/230.5; 544/71; 544/92
[58] Field of Search .................. 544/89, 92, 71; 514/229.8, 230.5

[56] References Cited

U.S. PATENT DOCUMENTS 2,943,087 6/1960 Ohnacker et al. ............ 544/92
4,341,778 7/1982 Mentrup et al. ............ 514/229.8

FOREIGN PATENT DOCUMENTS 1173101 7/1964 Fed. Rep. of Germany .

OTHER PUBLICATIONS

Grant and Hackh's Chemical Dictionary, 5th ed., 1984, p. 53.
New et al., Chem. Abs., vol. 54 (5), Entry #4818i (1960).
Stamm et al., Chem. Abs. vol. 61 (10), Entry #12012g (1964).
Finkelstein et al., J. Med. Chem., vol. 11, pp. 1038–1040 (1968).

Primary Examiner—Mukund J. Shah
Assistant Examiner—E. C. Ward

Attorney, Agent, or Firm—Dressler, Goldsmith, Shore, Sutker & Milnamow, Ltd.

[57] ABSTRACT

The invention relates to the new 3-arylalkylaminoalkyl-4H-1,3-benzoxazin-4-one derivatives of general formula

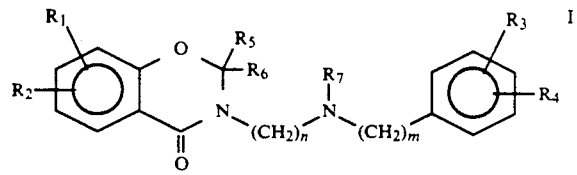

in which:

$R_1$, $R_2$, $R_3$ and $R_4$, which may be identical or different, denote a hydrogen, a branched or unbranched lower alkyl group or an alkyloxy, halo, nitro, amino, acylamino or dialkylamino group, and $R_1$ and $R_2$ on one hand and $R_3$, $R_4$ on the other hand can fuse to give a divalent group and more especially —$OCH_2O$—, —$OCH_2CH_2O$— and —$CH=CH—CH=CH$—; $R_5$ and $R_6$, which may be identical or different, denote a hydrogen, a saturated or unsaturated, branched or unbranched alkyl group containing from 1 to 15 carbon atoms or a cycloalkyl group, and $R_5$ and $R_6$ can fuse to give a —$(CH_2)_p$—group with p=2 to 7; $R_7$ denotes a hydrogen, a saturated or unsaturated, branched or unbranched alkyl group containing from 1 to 15 carbon atoms, a cycloalkyl group, a substituted or unsubstituted aryl and a substituted or unsubstituted arylalkyl; the values of m and n, which may be identical or different, can vary from 1 to 4 inclusive; as well as the therapeutically acceptable organic or inorganic salts of I. The compounds are useful as medicinal products in the treatment of disorders of the cardiovascular system.

7 Claims, No Drawings

2,3-DIHYDRO-3-ARYLALKYLAMINOALKYL-4H-1,3-BENZOXAZIN-4-ONE DERIVATIVES, THEIR PREPARATION AND THEIR APPLICATION AS MEDICINAL PRODUCTS WHICH ARE USEFUL IN THERAPY

The present invention, carried out at the PIERRE FABRE Research Center, relates to the synthesis of 3-alkylaminoalkyl-1,3-benzoxazin-4-one derivatives of novel structure I or their salts and to their use as a medicinal product, in particular in cardiovascular therapy.

In contrast to their nitrogen analogs (quinazolones), 1,3-benzoxazin-4-ones have been studied relatively little. Only a few derivatives, mostly substituted at the 2-position, have been claimed, and led to the marketing of chlorothenoxazine which has been used as an antiinflammatory/antipyretic (see U.S. Pat. No. 2,943,087, CA 54, 2 4818 i (1960), Kadatz R., Arzneim. Forsch. 7 651 (1957)).

The activities of these derivatives are of the same order as those of the salicylamide precursor.

A few other derivatives substituted on the aromatic ring and on the nitrogen have not given any noteworthy pharmacological result (see J. Finkelstein and E. Chiang J. Med. Chem. 11, 1038 (1968), and in particular 3-(2-diethylaminoethyl)-2,3-dihydro-4H-1,3-benzoxazin-4-one which was inactive). Substitution on the nitrogen of 2,3-dihydro-4H-1,3-benzoxazin-4-one with an arylalkylaminoalkyl group leads to derivatives of novel structure I which exhibit a potent bradycardic and antiarrhythmic activity combined with a substantial antiischemic and moderate calcium-inhibitory effect.

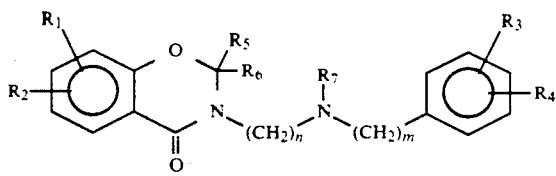

Molecules Claimed

The novel derivatives of structure I which are the subjects of the present invention are defined as follows:

. $R_1$, $R_2$, $R_3$ and $R_4$, which may be identical or different, denote a hydrogen, a branched or unbranched $C_{1-6}$ lower alkyl group, an alkyloxy, a halogen or a nitro, amino, acylamino or dialkylamino group and, by way of non-limiting examples: H, Me, Et, i-Pr, MeO, EtO, Br, Cl, F, $NO_2$, $NH_2$, $CH_3CONH$, $ME_2N$; finally, $R_1R_2$ on the one hand and $R_3R_4$ on the other hand can fuse in pairs to form a $-OCH_2O-$, $-OCH_2CH_2O-$ or $-CH=CH-CH=CH-$ group;

$R_5$ and $R_6$, which may be identical or different, denote a hydrogen, a saturated or unsaturated, branched or unbranched alkyl group containing from 1 to 15 carbon atoms or a cycloalkyl group containing from 3 to 8 carbon atoms and, in particular, H, Me, Et, i-Pr, n-heptyl, n-undecyl, n-pentadecyl, allyl, cyclohexyl radicals. Finally, $R_5$ and $R_6$ can fuse to give a polymethylene group $-(CH_2)_p-$, with p able to assume values from 2 to 7;

$R_7$ denotes a hydrogen, a saturated or unsaturated, branched or unbranched alkyl group containing from 1 to 6 carbon atoms, a cycloalkyl group containing from 3 to 8 carbon atoms, a substituted or unsubstituted aryl group composed of 6 to 10 carbon atoms or an arylalkyl group containing from 7 to 15 carbon atoms and, in particular, H, Me, Et, i-Pr, n-hexyl, allyl, cyclohexyl, phenyl, benzyl, phenethyl, 4-methoxyphenyl, 3,4-dimethoxyphenethyl, 4-chlorophenethyl radicals;

the values of m and n, which may be identical or different, can vary from 1 to 4 inclusive.

The present invention also includes the therapeutically acceptable inorganic or organic salts of the claimed compound I which are water-soluble and enable the medicinal product to be administered in injectable form when water is present. The following salts are given by way of non-limiting examples: hydrochloride, hydrobromide, mesylate, sulfate, phosphate, succinate, maleate, fumarate, citrate, tartrate, lactate, pamoate, pyroglutamate or the like.

The present invention also relates to the use of the compounds of general formula I by way of a medicinal product and to the pharmaceutical compositions containing this medicinal product. The pharmaceutical compositions according to the present invention can employ one or more compounds of formula I, optionally in combination with one or more active principles. Finally, the processes for the synthesis of the compounds of general formula I also form part of the present invention.

Synthesis of the Compounds of General Structure I

Two general synthesis routes can be used for preparing the compounds of formula I:

a) Final cyclization

Method A

Final cyclization is performed starting with the salicylamide precursors of general formula II, by cyclocondensation with formaldehyde in the form of trioxymethylene, paraformaldehyde, or paraldehyde or an aliphatic aldehyde, an arylaliphatic, aromatic or cyclic aldehyde or an activated or non-activated ketone III in the form of an acetal, according to the equation A:

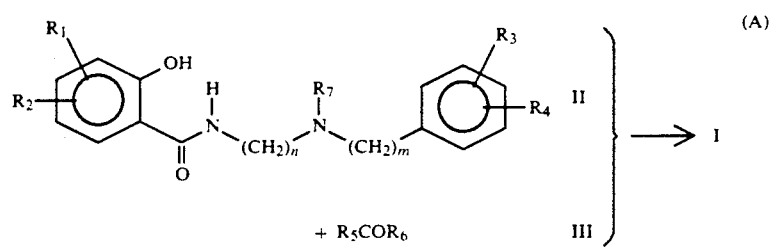

In the intermediates of general formulae II and III, $R_1$ to $R_7$, m and n have the same meaning as in the final compound I.

The reaction must be carried out in a strong acid medium such as, for example, hydrochloric acid to activate the carbonyl, and in a protic organic solvent and preferably in acetic acid. It is desirable to use an aprotic cosolvent such as chloroform or, preferably, ethyl acetate in the case where the salicylic acid is substituted with labile groups. The reaction is carried out at between 25° and 50° and the reaction time varies from 15 min to 2 h. The salicylamides are prepared either by transamidation or by direct condensation of the salicylic acids with the appropriately substituted diamines, activating the acids in the form of a chloride or of mixed anhydrides or using a dehydrating agent such as DCC in the presence or absence of HOBT.

Method B

When the radical $R_5$ or $R_6$ is an aromatic radical directly linked to the carbonyl, it is preferable to prepare the Schiff's base obtained by reacting this carbonyl derivative with the corresponding diamine and to condense it with the appropriately substituted salicylic acid chloride according to the reaction B:

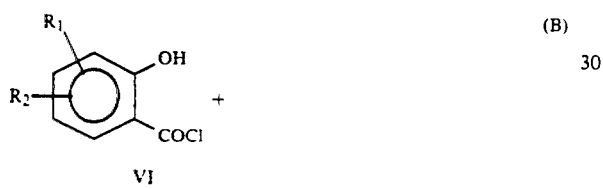

(B)

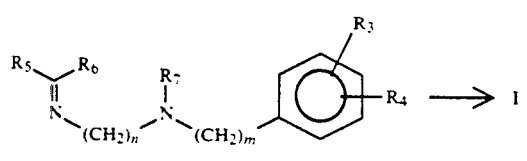

In the intermediates of general formulae VI and VII, $R_1$ to $R_4$, $R_7$, m and n have the same meaning as in the compound of formula I.

The condensation is preferably carried out in the heated state in an apolar solvent such as toluene.

b) Final Alkylation

Method C

The introduction of the amine group may be carried out at the end by condensation of the activated alcohol IV with the amine V according to the reaction C:

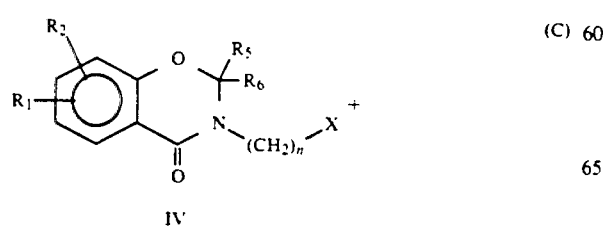

(C)

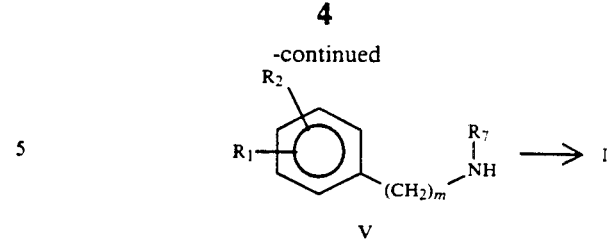

where $R_1$ to $R_7$, n and m have the same meaning as in I and where X denotes a halogen (Cl, Br, I) or a mesylate ($MeSO_3$—) or tosylate ($CH_3C_6H_4SO_3$—) group. The condensation is preferably carried out at 25° C. in DMF in the presence of a tertiary amine. This method enables, in particular, the compounds I in which $R_7$=H to be prepared. The final compound trisubstituted on the nitrogen may be obtained either directly, or from the secondary amine I ($R_7$=H) by alkylation with a group $R_7$—X where X denotes a halogen or a sulfate group, or by alkylating according to the Eschweiler-Clarke reaction with the system formic acid/aldehyde derived from $R_7$.

The intermediates IV of novel structure also form the subject of the present invention.

The above bases may be salified with an equimolecular amount of desired acid, using an apolar or polar solvent such as ethyl acetate or ethanol, by way of non-limiting examples.

EXAMPLE 1 (F 3151)

2,3-Dihydro-3-{3-[(methyl)(3,4-dimethoxyphenethyl)amino]propyl}-4H-1,3-benzoxazin-4-one hydrochloride (compound A)

A solution of 2 g (5.37 mmol) of N-{3-[(methyl)(3,4-dimethoxyphenethyl)amino]propyl}salicylamide in 18 ml of chloroform and 1 ml of acetic acid is treated for 2 min with a stream of gaseous hydrochloric acid. 340 milligrams of trioxymethylene are then added to the above mixture, which is heated for 20 min to 70°-75° C. After return to room temperature, a stream of nitrogen is passed through for 30 min and the mixture is then filtered on a sinter and evaporated to dryness. The residue is taken up in toluene and re-evaporated to dryness in a rotary evaporator under vacuum. The solid residue (3.10 g) is ground in isopropyl ether and filtered. The cream powder obtained (m=2.1 g) is recrystallized in a 75:25 i-PrOH/EtOH mixture to give 1.53 g (yld=68%) of compound A of formula:

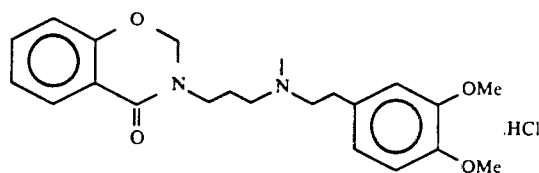

Compound A empirical formula: $C_{22}H_{29}ClN_2O_4$
molecular mass: 420.94
white crystals
melting point: 167°-169° C.
thin-layer chromatography on Merck silica gel 60 F 254
. eluent: $CHCl_3$/MeOH/$NH_4OH$, 90:9:1
. Rf: 0.57

IR (KBr) √CO amide: 1650 cm$^{-1}$
NMR (CDCl$_3$) δ: 5.17 (s, 2H, —OCH$_2$N—), 2.75 (d, 3H, CH$_3$—NH—)
solubility: soluble to the extent of 10% in water.

EXAMPLE 2 (F 3226)

2,3-Dihydro-6,7-dimethoxy-3-{3-[(methyl)(3,4-dimethoxyphenethyl)amino]propyl}-4H-1,3-benzoxazin-4-one hydrochloride (compound B)

A mixture of 1.5 g (3.5 mmol) of 3,4-dimethoxy-N-{3-[(methyl)(3,4-dimethoxyphenethyl)amino]propyl}salicylalmide in 20 ml of acetic acid and 25 ml of a 2N solution of HCl in AcOEt is treated with 1.1 g of trioxymethylene. After 3 h of stirring at 20° C., the mixture is taken to an oil bath at 50° for 2 h and then evaporated to dryness in a rotary evaporator under vacuum. The solid residue (m=1.9 g) is purified directly on a silica column (60 g) eluting with a 95:4.5:0.5 CHCl$_3$/MeOH/NH$_4$OH mixture. The fractions containing the expected derivative are combined and evaporated to dryness (m=1.7 g), and the residue is then taken up in an isopropyl alcohol/ethyl acetate mixture and converted to hydrochloride with a 2N solution of HCl in AcOEt to give 1.2 g (Yld=40%) of the compound B of formula:

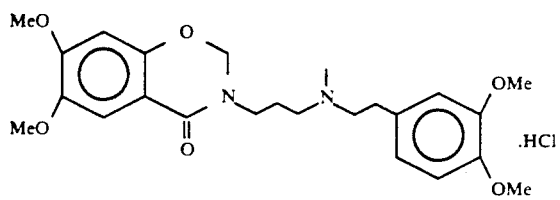

Compound B empirical formula: C$_{24}$H$_{33}$ClN$_2$O$_6$
molecular mass: 480.99
white crystals
melting point: 174° C.
thin-layer chromatography on Merck silica gel 60 F 254
. eluent: CHCl$_3$/MeOH/NH$_4$OH, 90:9:1
. Rf: 0.55
IR (KBr): √CO amide: 1650 cm$^{-1}$
NMR (CDCl$_3$) δ: 2.6 (s, 3H, CH$_3$NH), 5.05 (s, 2H, —OCH$_2$—N)
solubility: soluble to the extent of more than 10% in water.

EXAMPLE 3 (F 3262.01)

2,3-Dihydro-3-{3-[(methyl)(3,4-dimethoxyphenethyl)amino]propyl}-8-methoxy-4H-1,3-benzoxazin-4-one hydrochloride (compound C)

Starting with 3-methoxy-N-{3-[(methyl)(3,4-dimethoxyphenethyl)amino]propyl}salicylamide and using the preparation procedure described for the derivative B, the compound C of formula:

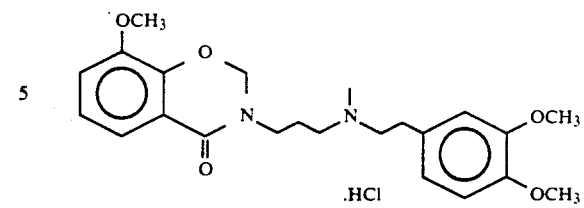

is obtained in a 25% yield.

Compound C empirical formula: C$_{23}$H$_{31}$ClN$_2$O$_5$
molecular mass: 450.96
white crystals
melting point: 143° C.
thin-layer chromatography on Merck silica gel 60 F 254
. eluent: CHCl$_3$/MeOH/NH$_4$OH, 90:9:1
. Rf: 0.65
IR (KBr): √CO amide: 1650 cm$^{-1}$
NMR (CDCl$_3$) δ: 2.75 (s, 3H, CH$_3$NH—), 5.15 (s, 2H, —OCH$_2$N)
solubility: soluble to the extent of approximately 10% in water.

EXAMPLE 4 (F 3297)

2,3-Dihydro-3-{3-[(methyl)(3,4-dimethoxyphenethyl)amino]propyl}-6-methoxy-4H-1,3-benzoxazin-4-one hydrochloride (compound D)

Starting with 5-methoxy-N-{3-[(methyl)(3,4-dimethoxyphenethyl)amino]propyl}salicylamide and using the synthesis procedure described for B, the compound D of structure:

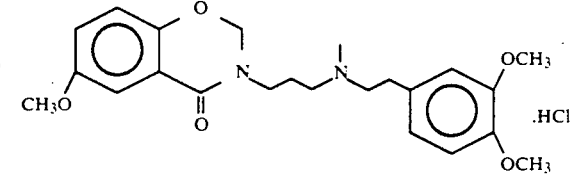

is obtained in a 56% yield.

Compound D empirical formula: C$_{23}$H$_{31}$ClN$_2$O$_5$
molecular mass: 450.96
white crystals
melting point: 142° C.
thin-layer chromatography on Merck silica gel 60 F 254
. eluent: CHCl$_3$/MeOH/NH$_4$OH, 90:9:1
. Rf: 0.70
IR (KBr): √CO amide: 1660 cm$^{-1}$
NMR (CDCl$_3$) δ: 2.85 (d, 3H, CH$_3$NH), 5.05 (s, 2H, —OCH$_2$N—)
solubility in water: >10%

EXAMPLE 5 (F 3311)

2,3-Dihydro-3-{3-[(methyl)(3,4-dimethoxyphenethyl)amino]propyl}-7-methoxy-4H-1,3-benzoxazin-4-one hydrochloride (compound E)

A mixture composed of 1.35 g (4.2 mmol) of 2,3-dihydro-7-methoxy-3-[3-(methanesulfonyloxy)propyl]-4H-1,3-benzoxazin-4-one of formula:

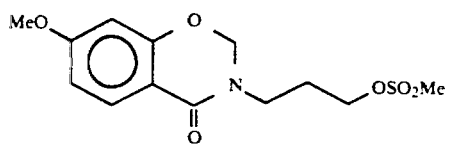

Empirical formula: $C_{13}H_{17}NO_6$
Molecular mass: 315.34
White crystals
NMR (CDCl$_3$) δ: 2.95 (s, 3H, C$\underline{H}_3$SO$_3$), 3.7 (s, 3H, C$\underline{H}_3$O), 5.0 (s, 2H, —OC$\underline{H}_2$N—)—) and 1.46 g (6.3 mmol) of N-methylhomoveratrylamine hydrochloride in 10 ml of triethylamine is diluted with 20 ml of pure reagent grade DMF and taken to an oil bath at 50° for 10 h. The crude mixture is diluted with water and extracted several times with ethyl acetate, and the organic phase thereby obtained is washed with water and with saline solution, dried over sulfate and evaporated to dryness. The residue (1.2 g) is purified on an open column of silica (25 g), eluting with a 95:4.5:0.5 CHCl$_3$/MeOH/NH$_4$OH mixture. The fractions containing the expected compound are combined and evaporated to dryness, and the residual oil is then taken up in AcOEt and converted to hydrochloride with a 2N solution of HCl in AcOEt to give 550 mg (Yld: 30%) of compound E of formula:

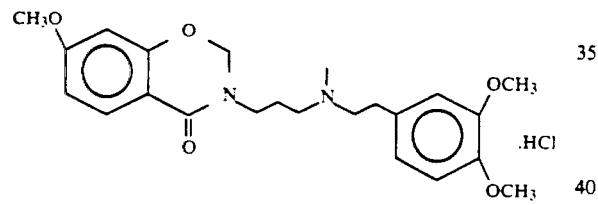

Compound E
empirical formula: $C_{23}H_{31}ClN_2O_5$
molecular mass: 450.96
white crystals
melting point: 148° C.
thin-layer chromatography on Merck silica gel 60 F 254
 . eluent: CHCl$_3$/MeOH/NH$_4$OH, 90:9:1
 . Rf: 0.61
IR (KBr): √CO amide: 1665 cm$^{-1}$
NMR (CDCl$_3$) δ: 2.75 (d, 3H, C$\underline{H}_3$NH), 5.05 (s, 2H, —OC$\underline{H}_2$N—)
soluble in water to the extent of 10%.

EXAMPLE 6 (F 3265)

2,3-Dihydro-3-{3-[(methyl)(3,4-dimethoxyphenethyl)amino]propyl}-6-methyl-4H-1,3-benzoxazin-4-one hydrochloride (compound F)

Starting with 5-methyl-N-{3-[(methyl)(3,4-dimethoxyphenethyl)amino]propyl}salicylamide and using the synthesis process described in Example 2, the compound F of structure:

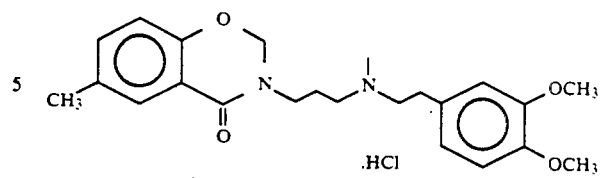

is obtained in a 57% yield.

Compound F
empirical formula: $C_{23}H_{31}ClN_2O_4$
molecular mass: 434.96
white crystals
melting point: 147° C.
thin-layer chromatography on Merck silica gel 60 F 254
 . eluent: CHCl$_3$/MeOH/NH$_4$OH, 90:9:1
 . Rf: 0.65
IR (KBr): √CO amide: 1650 cm$^{-1}$
NMR (CDCl$_3$) δ: 2.8 (s, 3H, C$\underline{H}_3$NH), 5.06 (s, 2H, OC$\underline{H}_2$N)
solubility in water in the region of 10%.

EXAMPLE 7 (F 3266)

2,3-Dihydro-3-{3-[(methyl)(3,4-dimethoxyphenethyl)amino]propyl}-7-methyl-4H-1,3-benzoxazin-4-one hydrochloride (compound G)

Starting with 4-methyl-N-{3-[(methyl)(3,4-dimethoxyphenethyl)amino]propyl}salicylamide and using the synthesis process described in Example 2, the compound G of structure:

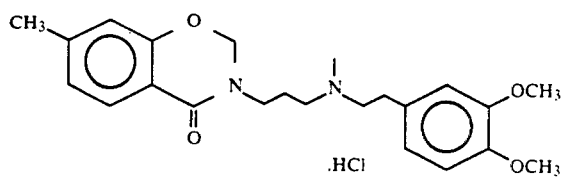

is obtained in a 35% yield.

Compound G
empirical formula: $C_{23}H_{31}ClN_2O_4$
molecular mass: 434.96
white crystals
melting point: 148° C.
thin-layer chromatography on Merck silica gel 60 F 254
 . eluent: CHCl$_3$/MeOH/NH$_4$OH, 90:9:1
 . Rf: 0.59
IR (KBr): √CO amide: 1660 cm$^{-1}$
NMR (CDCl$_3$) δ: 2.8 (s, 3H, C$\underline{H}_3$NH), 5.08 (s, 2H, —OC$\underline{H}_2$N—)
soluble in water to the extent of 9%.

EXAMPLE 8 (F 3267)

2,3-Dihydro-3-{3-[(methyl)(3,4-dimethoxyphenethyl)amino]propyl}-8-methyl-4H-1,3-benzoxazin-4-one hydrochloride (compound H)

In a manner similar to the process described in Example 2 and using 3-methyl-N-{3-[(methyl)(3,4-dimethoxyphenethyl)amino]propyl}salicylamide, the compound H of structure:

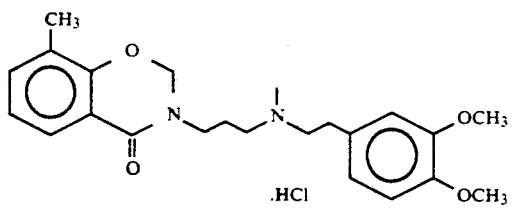

is prepared in a 50% yield.

Compound H empirical formula: $C_{23}H_{31}ClN_2O_4$
molecular mass: 434.96
white crystals
melting point: 149° C.
thin-layer chromatography on Merck silica gel 60 F 254
  . eluent: $CHCl_3/MeOH/NH_4OH$, 90:9:1
  . Rf: 0.60
IR (KBr): $\sqrt{}CO$ amide: 1660 cm$^{-1}$
NMR (CDCl$_3$) δ: 2.8 (s, 3H, C$\underline{H}_3$NH), 5.1 (s, 2H, —OC$\underline{H}_2$N—)
soluble to the extent of 8% in water.

EXAMPLE 9 (F 3263)

7-Chloro-2,3-dihydro-3-{3-[(methyl)(3,4-dimethoxyphenethyl)amino]propyl}-4H-1,3-benzoxazin-4-one hydrochloride (compound J)

Using 4-chloro-N-{3-[(methyl)(3,4-dimethoxyphenethyl)amino]propyl}salicylamide and employing the process described in Example 2, the compound J of structure:

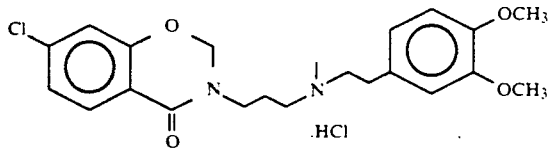

is obtained in a 35% yield.

Compound J empirical formula: $C_{22}H_{28}Cl_2N_2O_4$
molecular mass: 455.38
white crystals
melting point: 158° C.
thin-layer chromatography on Merck silica gel 60 F 254
  . eluent: $CHCl_3/MeOH/NH_4OH$, 90:9:1
  . Rf: 0.64
IR (KBr): $\sqrt{}CO$ amide: 1660 cm$^{-1}$
NMR (CDCl$_3$) δ: 2.83 (s, 3H, C$\underline{H}_3$NH), 5.2 (s, 2H, —OC$\underline{H}_2$—N—)
soluble to the extent of 12% in water.

EXAMPLE 10 (F 3264)

6-Bromo-2,3-dihydro-3-{3-[(methyl)(3,4-dimethoxyphenethyl)amino]propyl}-4H-1,3-benzoxazin-4-one hydrochloride (compound K)

Starting with 5-bromo-N-{3-[(methyl)(3,4-dimethoxyphenethyl)amino]propyl}salicylamide and using the preparation process of Example 2, the compound K of general structure:

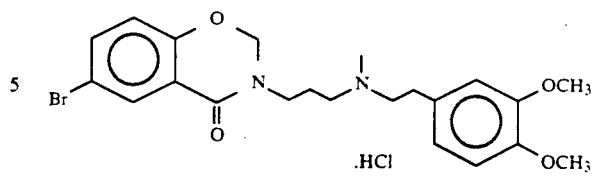

is prepared in a 45% yield.

Compound K empirical formula: $C_{22}H_{28}BrClN_2O_4$
molecular mass: 499.84
white crystals
melting point: 159° C.
thin-layer chromatography on Merck silica gel 60 F 254
  . eluent: $CHCl_3/MeOH/NH_4OH$, 90:9:1
  . Rf: 0.68
IR (KBr): $\sqrt{}CO$ amide: 1660 cm$^{-1}$
NMR (CD$_3$OD) δ: 2.78 (s, 3H, C$\underline{H}_3$NH), 5.07 (s, 2H, —OC$\underline{H}_2$N—)
soluble to the extent of 9% in water.

EXAMPLE 11 (F 3296)

2,3-Dihydro-3-{3-[(methyl)(3,4-dimethoxyphenethyl)amino]propyl}-8-methoxy-2-methyl-4H-1,3-benzoxazin-4-one hydrochloride (compound L)

Starting with 3-methoxy-N-{3-[(methyl)(3,4-dimethoxyphenethyl)amino]propyl}salicylamide, replacing trioxymethylene by paraldehyde and using the preparation process of Example 2, the compound L of formula:

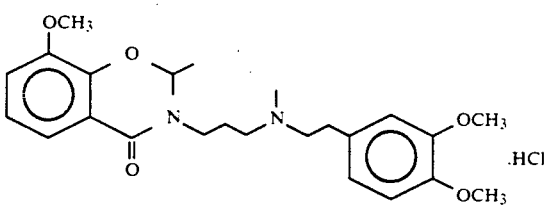

is prepared in a 55% yield.

Compound L empirical formula: $C_{24}H_{33}ClN_2O_5$
molecular mass: 464.99
white crystals
melting point: 158° C.
thin-layer chromatography on Merck silica gel 60 F 254
  . eluent: $CHCl_3/MeOH/NH_4OH$, 90:9:1
  . Rf: 0.72
IR (KBr): $\sqrt{}CO$ amide: 1665 cm$^{-1}$
NMR (CDCl$_3$) δ: 1.9 (d, 3H, CH$_3$CH), 2.8 (d, 3H, CH$_3$NH), 5.4 (5 m, 1H, —C$\underline{H}$—CH$_3$)
soluble to the extent of 10% in water.

EXAMPLE 12 (F 3298)

2,3-Dihydro-6,7-dimethoxy-3-{3-[(methyl)(3,4-dimethoxyphenethyl)amino]propyl}-2-methyl-4H-1,3-benzoxazin-4-one hydrochloride (compound M)

Applying the procedure of Example 2 and using the same substituted salicylamide, but replacing trioxymethylene by paraldehyde, the derivative methylated at the 2-position of B, that is to say the compound M of formula:

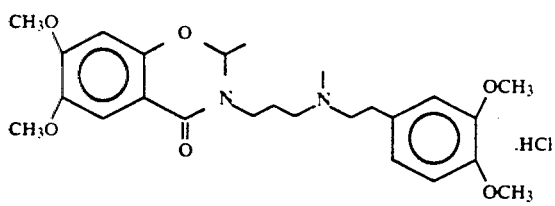

is prepared in a 70% yield.

Compound M empirical formula: $C_{25}H_{35}ClN_2O_6$
molecular mass: 495.016
white crystals
melting point: 149° C.
thin-layer chromatography on Merck silica gel 60 F 254
  . eluent: $CHCl_3/MeOH/NH_4OH$, 90:9:1
  . Rf: 0.70
IR (KBr): $\sqrt{}CO$ amide: 1655 cm$^{-1}$
NMR (CDCl$_3$) δ: 1.85 (d, 3H. C$\underline{H}_3$CH), 2.74 (d, 3H, C$\underline{H}_3$NH), 5.25 (m, 1H, —C$\underline{H}$CH$_3$)
soluble to the extent of 10% in water.

EXAMPLE 13 (F 3299)

2,3-Dihydro-6,7-dimethoxy-3-{3-[(methyl)(dimethoxyphenethyl)amino]propyl}-2-n-heptyl-4H-1,3-benzoxazin-4-one hydrochloride (compound N)

Using the procedure of Example 2 and starting with the same substituted salicylamide, but replacing trioxymethylene by n-octanal, the derivative N of formula:

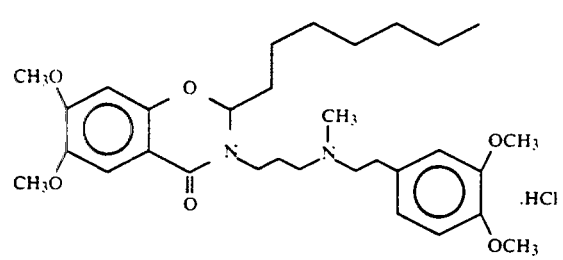

is prepared in a 58% yield.

Compound N empirical formula: $C_{31}H_{47}ClN_2O_6$
molecular mass: 579.186
pale beige crystals
melting point: 117° C.
thin-layer chromatography on Merck silica gel 60 F 254
  . eluent: $CHCl_3/MeOH/NH_4OH$, 90:9:1
  . Rf: 0.75
IR (KBr): $\sqrt{}CO$ amide: 1660 cm$^{-1}$
NMR (CDCl$_3$) δ: 2.75 (d, 3H. C$\underline{H}_3$NH), 5.2 (m, 1H, —C$\underline{H}$CH$_2$—)
soluble to the extent of 10% in water.

EXAMPLE 14 (F 3310)

2,3-Dihydro-6,7-dimethoxy-3-{3-[(methyl)(phenethyl)amino]propyl}-4H-1,3-benzoxazin-4-one hydrochloride (compound O)

Starting with 4,5-dimethoxy-N-{3-[(methyl)(phenethyl)amino]propyl}salicylamide and using the procedure described in Example 9 without column purification, the compound O of structure:

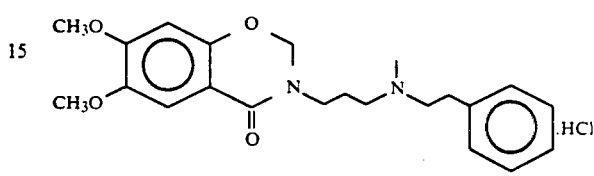

is obtained directly in an 85% yield.

Compound O empirical formula: $C_{22}H_{29}ClN_2O_4$
molecular mass: 420.946
white crystals
melting point: 174° C.
thin-layer chromatography on Merck silica gel 60 F 254
  . eluent: $CHCl_3/MeOH/NH_4OH$, 90:9:1
  . Rf: 0.65
IR (KBr): $\sqrt{}CO$ amide: 1670 cm$^{-1}$
NMR (CDCl$_3$) δ: 2.8 (s, 3H, C$\underline{H}_3$NH), 5.06 (s, 2H, —OC$\underline{H}_2$N—)
soluble to the extent of more than 10% in water.

EXAMPLE 15 (F 3325)

2,3-Dihydro-6,7-dimethoxy-3-[3-(3,4-dimethoxyphenethylamino)propyl]-4H-1,3-benzoxazin-4-one hydrochloride (compound P)

2,3-Dihydro-6,7-dimethoxy-3-[3-(methanesulfonyloxy)propyl]-4H-1,3-benzoxazin-4-one of formula:

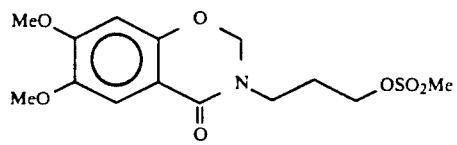

empirical formula: $C_{14}H_{19}NO_7S$
molecular mass: 345.37
white crystals
melting point: 123° C.
IR (KBr): $\sqrt{}CO$ amide: 1660 cm$^{-1}$, $\sqrt{}SO_3$ 1360, 1180 cm$^{-1}$
NMR (CDCl$_3$) δ: 2.73 (s. 3H, C$\underline{H}_3$SO$_3$), 5 (s, 2H, OC$\underline{H}_2$N)
is condensed in a 70% yield with excess homoveratrylamine according to the procedure described in Example 5, to give the compound P of formula:

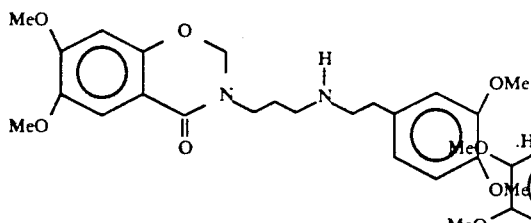
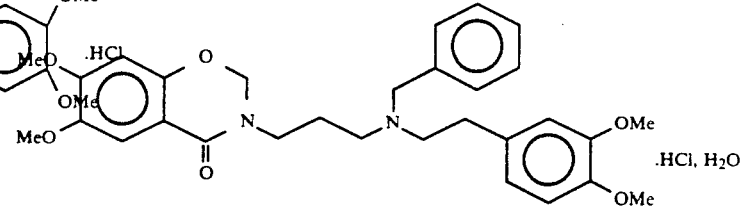

Compound P empirical formula: $C_{23}H_{31}ClN_2O_6$
molecular mass: 466.962
white crystals
melting point: 155° C.
thin-layer chromatography on Merck silica gel 60 F 254
. eluent: $CHCl_3/MeOH/NH_4OH$, 90:9:1
. Rf: 0.43
IR (KBr): $\sqrt{}CO$ amide: 1645 cm$^{-1}$
NMR (CDCl$_3$) δ: 5.00 (s, 2H, —OCH$_2$N—)
soluble to the extent of more than 10% in water.

EXAMPLE 16

2,3-Dihydro-6,7-dimethoxy-3-{3-[(methyl)(3,4-dimethoxyphenethyl)amino]propyl}-4H-1,3-benzoxazin-4-one hydrochloride (compound B)

Starting with the intermediate 2,3-dihydro-6,7-dimethoxy-3-[3-(methanesulfonyloxy)propyl]-4H-1,3-benzoxazin-4-one prepared as in Example 15, but condensing it with N-methyl-3,4-dimethoxyphenethylamine as in Example 15, the compound B, the physicochemical characteristics of which are identical to those described in Example 2, is obtained in a 68% yield.

EXAMPLE 17

2,3-Dihydro-6,7-dimethoxy-3-{3-[(benzyl)(3,4-dimethoxyphenethyl)amino]propyl}-4H-1,3-benzoxazin-4-one hydrochloride monohydrate (compound O)

A solution of 2.2 g (4.7 mmol) of 2,3-dihydro-6,7-dimethoxy-3-[3-(3,4-dimethoxyphenethylamino)propyl]-4H-1,3-benzoxazin-4-one hydrochloride, prepared as described in Example 15, in 25 ml of pure reagent grade DMF is cooled in an ice bath and then treated with 3 ml of triethylamine and then with 0.88 g (5.2 mmol) of benzyl bromide, and stirred for 1 h at 0° C. and then 5 h at 25° C. The mixture is evaporated to dryness under vacuum and then taken up in 50 ml of water, cooled and brought to pH 9 by adding 30% caustic soda solution. The base is extracted several times with ethyl acetate. The organic phase thereby obtained is washed with water and with saline solution, and dried over sodium sulfate and then evaporated to dryness. The residual oil (2.45 g) is purified on an open silica column (50 g), eluting with a 95:5 CHCl$_3$/MeOH mixture. The fractions containing the expected derivative are combined, evaporated to dryness, then taken up in ether and converted to hydrochloride with a 2N solution of HCl in AcOEt, to give 1.75 g (Yld: 68%) of compound Q of formula:

Compound O empirical formula: $C_{30}H_{39}ClN_2O_7$
molecular mass: 575.10
pale beige amorphous powder
slow melting point: 78°–82° C.
thin-layer chromatography on Merck silica gel 60 F 254
. eluent: $CHCl_3/MeOH/NH_4OH$, 90:9:1
. Rf: 0.76
IR (KBr): $\sqrt{}CO$ amide: 1660 cm$^{-1}$
soluble to the extent of 6% in water.

EXAMPLE 18

2,3-Dihydro-6,7-dimethoxy-3-{3-[(methyl)(3,4-dimethoxyphenethyl)amino]propyl}-4H-1,3-benzoxazin-4-one hydrochloride (compound B)

8 g (18.5 mmol) of base of the compound P are dissolved with cooling in 2.1 ml (56 mmol) of formic acid, stirred for 10 min, then treated at 25° C. in 1.6 ml of 40% strength formaldehyde (23 mmol) and then taken for 10 min to an oil bath preheated to 80° C. The mixture is cooled, taken up in methylene chloride and alkalinized with caustic soda solution. The phases are separated, the aqueous phase is re-extracted with the same solvent and the organic phases are combined, washed with saline solution and then dried and evaporated. The residue is converted to hydrochloride as in Example 2, to give the compound B, possessing the same characteristics as those described in Example 2, in a 90% yield.

EXAMPLE 19 (F 3326)

2,3-Dihydro-6,7-dimethoxy-3-[2-(3,4-dimethoxyphenethylamino)ethyl]-4H-1,3-benzoxazin-4-one hydrochloride (compound R)

Starting with 2,3-dihydro-6,7-dimethoxy-3-[2-(methanesulfonyloxy)ethyl]-4H-benzoxazinone of formula:

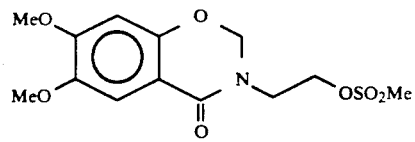

empirical formula: $C_{13}H_{17}NO_7S$
molecular mass: 331.34
off-white crystals
melting point: 135° C.
IR (KBr): $\sqrt{}CO$ 1660, MeSO$_3$R 1350 and 1180 cm$^{-1}$
NMR (CDCl$_3$) δ: 2.8 (s, 3H, CH$_3$SO$_3$), 5.2 (s, 2H, —OCH$_2$N)

and condensing it with excess homoveratrylamine according to the process described in Example 15 or 16, the compound R of formula:

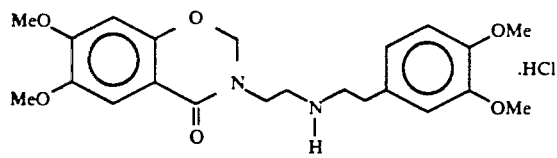

is obtained in a 60% yield.

Compound R empirical formula: $C_{22}H_{29}ClN_2O_6$
molecular mass: 452.94
white crystals
melting point: 198° C.
thin-layer chromatography on Merck silica gel 60 F 254
. eluent: $CHCl_3/MeOH/NH_4OH$, 90:9:1
. Rf: 0.58
IR (KBr): $\sqrt{}CO$ amide: 1665 cm$^{-1}$
NMR (CDCl$_3$) δ: 5.2 (s, 2H, —OCH$_2$N—)
soluble to the extent of 12% in water.

EXAMPLE 20 (F 3327)

2,3-Dihydro-6,7-dimethoxy-3-{2-[(methyl)(3,4-dimethoxyphenethyl)amino]ethyl}-4H-1,3-benzoxazin-4-one hydrochloride (compound S)

Starting with the previous intermediate, 2,3-dihydro-6,7-dimethoxy-3-[2-(methanesulfonyloxy)ethyl]-4H-1,3-benzoxazin-4-one, but condensing this product with N-methylhomoveratrylamine according to the procedure described in Example 5 or 15, the compound S of structure:

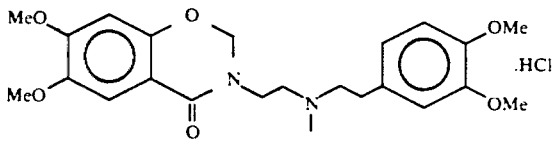

is prepared in a 65% yield.

Compound S empirical formula: $C_{23}H_{31}ClN_2O_6$
molecular mass: 466.96
white crystals
melting point: 140° C.
thin-layer chromatography on Merck silica gel 60 F 254
. eluent: $CHCl_3/MeOH/NH_4OH$, 90:9:1
. Rf: 0.65
IR (KBr): $\sqrt{}CO$ 1665 cm$^{-1}$
NMR (CDCl$_3$) δ: 2.83 (s, 3H, CH$_3$NH), 5.2 (s, 2H, —OCH$_2$N—)

Biological experiments

The compounds of the present invention of general formula I and their therapeutically acceptable salts with acids exhibit advantageous pharmacodynamic properties. In effect, these compounds are strongly bradycardic and moderately calcium-antagonistic. They act directly at cardiac level and are used as antianginals. They decrease the heart rate and oxygen consumption.

1) Toxicology

The chemical compounds described above were subjected to toxicity controls. This study was carried out on conventional mice weighing 20 to 22 g. The water-soluble salts of the compounds of general formula I were administered intravenously. The 50% lethal dose (LD$_{50}$) is calculated according to the method of Miller and Tainter (Proc. Soc. Exp. Biol. Med. 1944, 57, 261).

The relative LD$_{50}$ values of the compound A (Example 1) and B (Example 2) are given below by way of non-limiting examples.

TABLE 1

| Compound | LD$_{50}$ iv |
|---|---|
| A | 27 mg/kg |
| B | 48 mg/kg |

2) Pharmacological study

The pharmacological experiments to which the chemical molecules which are the subject of the present invention were subjected enabled an advantageous activity on the cardiovascular system to be demonstrated. The pharmacological activities were demonstrated in vivo and in vitro.

a) The technique of coronary ligation in anesthetized rats according to Clark et al. (J. Pharm. Methods 1980, 3, 357-368) was used to demonstrate the antiarrhythmic activity.

The results are given in Table II and are expressed as the percentage change in the heart rate relative to controls, 1 min and 10 min after injection of the compounds A, B, G, J and N associated with Examples 1, 2, 7, 9 and 13, given by way of non-limiting examples; SC denotes the percentage reduction in disorders of rhythm induced by these compounds, n denotes the number of animals.

TABLE II

| Compound (No. rats) | Dose mg/kg iv | % fall in heart rate after 1 min | % fall in heart rate after 10 min | % fall in arrhythmias |
|---|---|---|---|---|
| A (n = 5) | 2.5 | −30 | −11 | −9 |
| A (n = 5) | 10 | −50 | −19 | −76 |
| B (n = 7) | 2.5 | −50 | −28 | −38 |
| B (n = 7) | 10 | −66 | −60 | −80 |
| G (n = 7) | 2.5 | −39 | −16 | −1 |
| J (n = 7) | 2.5 | −32 | −12 | −37 |
| N (n = 5) | 2.5 | −4 | −6 | −72 | b) The bradycardic effect and the analysis of the intracardiac conduction times were studied on rats anesthetized with pentobarbital sodium (40 mg/kg ip) and left in spontaneous ventilation. The electrocardiogram is recorded simultaneously in the standard leads OI, OII and OIII; the arterial blood pressure is measured on a femoral artery. The percentage changes are considered at the peak of action. The results relating to the compounds A, B, J, G and N are given in Table III, by way of non-limiting example.

TABLE III

| Compound (No. rats) | Dose mg/kg iv | % ABP | HR | % modification of the ECG intervals PQ | QRS | QTS | TP |
|---|---|---|---|---|---|---|---|
| A (n = 10) | 3 | −33 | −31 | +26 | +11 | −29 | −76 |
| B (n = 7) | 1 | −16 | −32 | +9 | +12 | +38 | +95 |
| B (n = 7) | 3 | −34 | −55 | +17 | +24 | +75 | +211 |
| G (n = 5) | 1 | −10 | −18 | +10 | +5 | +12 | +32 |

TABLE III-continued

| Compound (No. rats) | Dose mg/kg iv | % ABP | HR | % modification of the ECG intervals | | | |
|---|---|---|---|---|---|---|---|
| | | | | PQ | QRS | QTS | TP |
| J (n = 5) | 1 | −13 | −16 | +9 | +12 | +12 | +29 |
| N (n = 5) | 1 | −9 | −12 | +7 | +12 | +10 | +21 |

ABP: mean arterial blood pressure
HR: heart rate
PQ: atrioventricular conduction time
QRS: intraventricular conduction time
QTC: Bazett's value
TP: electrocardiac diastole The bradycardic effect is also to be found in conscious dogs in which the heart rate is raised by the injection of hydralazine at a dose of 1 mg/kg iv according to the method of Kobinger and Lillie (Europ. J. Pharmacol. 1981, 72, 153-164). The administration of hydralazine causes tachycardia. When the latter has stabilized, the test products are injected intravenously.

The results are given in Table IV for the compounds A and B, by way of non-limiting examples:

TABLE IV

| Compound (No. of dogs) | Dose mg/kg iv | Heart rate (bts/min) | | |
|---|---|---|---|---|
| | | before | after | Change |
| A (n = 2) | 1 | 215 | 140 | −35% |
| B (n = 2) | 1 | 175 | 105 | −40% |

It should be noted that the compounds of the present invention do not induce bradycardia on dogs whose rhythm is normal.

c) Finally, the chronotropic and inotropic activities were measured on isolated guineapig atria placed in isolated organ cells. The organs are then connected to force gauges. The right atrium, beating in a spontaneous rhythm, enables the negative chronotropic effects of the products to be assessed. As regards the left atria, these are electrically stimulated at a fixed rhythm so as to evaluate actions on the inotropic effect.

The percentage changes are recorded in Table V for the compounds A, B, G and J, by way of non-limiting examples.

TABLE V

| Compound | Concentrations ug/ml | Right atrium, chronotropic effect | Left atrium, inotropic effect |
|---|---|---|---|
| A | 0.3 | −15 | −16 |
| A | 1 | −19 | −15 |
| B | 0.3 | −27 | −9 |
| B | 1 | −64 | −6.5 |
| G | 1 | −35 | −4 |
| J | 1 | −29 | −11 |

The compounds of the present invention are characterized by a favorable index, the bradycardic effect clearly prevailing over the weak cardiac depressant effect.

3) Therapeutic applications

In the light of their pharmacological activity, the derivatives of the present invention may be used in human and animal therapy in the treatment of cardiovascular disorders. These compounds induce a strong bradycardia associated with an antiarrhythmic effect. This bradycardia reduces oxygen consumption and increases the diastolic perfusion time and, on this basis, these compounds are useful as antianginals. Finally, they may be used as anti-ischemics since they decrease the disorders of rhythm resulting from ischemia.

The compounds of the present invention are used for preparing medicinal products which can be administered in warm-blooded animals or in man. The administration may be carried out orally, parenterally or rectally; each dose consists of an inert pharmaceutical adjuvant facilitating the preparation and absorption of the medicinal product, and of the active principle which can also be combined with another. These medicinal products may be presented in the form of tablets, gelatin capsules, suspensions, emulsions, syrups, suppositories, solutions or the like. The administration of the active principle of the present invention is carried out at an average dose of between 0.1 and 5 mg/kg of body weight.

Three preparations are given by way of non-limiting examples, it being possible for the ingredients as well as others to be introduced in other proportions without modifying the scope of the invention.

EXAMPLE 21

Injectable solution 2,3-Dihydro-6,7-dimethoxy-3-{3-[(methyl)(3,4-dimethoxyphenethyl)amino]propyl}-4H-1,3-benzoxazin-4-one hydrochloride: 5 mg
0.9% solution of NaCl in sterile distilled water: qs 2 ml stored in an ultraviolet-absorbing glass ampoule, and to be kept away from heat.

EXAMPLE 22

Tablets

| | |
|---|---|
| 2,3-Dihydro-6,7-dimethoxy-3-{3-[(methyl) (3,4-dimethoxyphenethyl)amino]propyl}- 4H-1,3-benzoxazin-4-one hydrochloride: | 50 mg |
| lactose: | 15 mg |
| corn starch: | 4 mg |
| polyvinylpyrrolidone: | 5 mg |
| magnesium stearate: | 1 mg |
| carboxymethylcellulose: | 15 mg |
| Total weight: | 90 mg |

EXAMPLE 23

Suppositories 2,3-Dihydro-6,7-dimethoxy-3-{3-[(methyl)(3,4-dimethoxyphenethyl)amino]propyl}-4H-1,3-benzoxazin-4-one hydrochloride: 120 mg suppository base (cocoa butter) qs 2.5 g to be kept away from light, heat and moisture.

| | |
|---|---|
| 2,3-Dihydro-6,7-dimethoxy-3-{3-[(methyl) (3,4-dimethoxyphenethyl)amino]propyl}- 4H-1,3-benzoxazin-4-one hydrochloride: | 120 mg |
| suppository base (cocoa butter) qs | 2.5 g |

I claim:

1. 2,3-dihydro-3-arylalkylaminoalkyl-4H-1,3-benzoxazin-4-one derivatives of formula I:

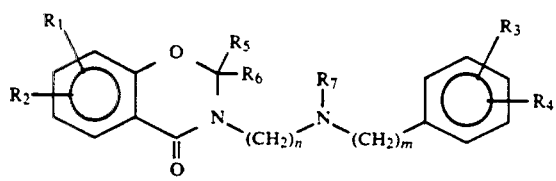

in which the substituents are defined as follows:

$R_1$, $R_2$, $R_3$ and $R_4$, which may be identical or different, denote a hydrogen, a branched or unbranched $C_{1-6}$ lower alkyl group or an alkyloxy, halo, nitro, amino, alkyl carboxylamino or dialkylamino group;

$R_5$ and $R_6$, which may be identical or different, denote a hydrogen, a saturated or unsaturated, branched or unbranched aliphatic group containing from 1 to 15 carbon atoms or a cycloalkyl group containing from 3 to 8 carbon atoms and where $R_5$ and $R_6$ can fuse to give a polymethylene group $-CH_2)_p-$, with p able to assume values from 2 to 7;

$R_7$ denotes a hydrogen, a saturated or unsaturated, branched or unbranched aliphatic group containing from 1 to 6 carbon atoms, a cycloalkyl group containing from 3 to 8 carbon atoms, a phenyl group, a phenylalkyl group having up to 9 carbon atoms in its alkyl substituent or a 4-methoxyphenyl, 3,4-dimethoxyphenethyl or a 4-chlorophenethyl radical;

the values of m and n, which may be identical or different, can vary from 1 to 4 inclusive, as well as the therapeutically acceptable organic or inorganic salts of I.

2. A compound which is chosen from the following compounds:

2,3-Dihydro-3-{3-[(methyl)(phenethyl)amino]propyl}-4H-1,3-benzoxazin-4-one hydrochloride 2,3-Dihydro-3-{3-[(methyl)(3,4-dimethoxyphenethyl)amino]propyl}-4H-1,3-benzoxazin-4-one hydrochloride 2,3-Dihydro-6,7-dimethoxy-3-{3-[(methyl)(3,4-dimethoxyphenethyl)amino]propyl}-4H-1,3-benzoxazin-4-one base 2,3-Dihydro-6,7-dimethoxy-3-{3-[(methyl)(3,4-dimethoxyphenethyl)amino]propyl}-4H-1,3-benzoxazin-4-one hydrochloride 2,3-Dihydro-6,7-dimethoxy-3-{3-[(methyl)(3,4-dimethoxyphenethyl)amino]propyl}-4H-1,3-benzoxazin-4-one hydrobromide 2,3-Dihydro-6,7-dimethoxy-3-{3-[(methyl)(3,4-dimethoxyphenethyl)amino]propyl}-4H-1,3-benzoxazin-4-one hydrogen maleate 2,3-Dihydro-6,7-dimethoxy-3-{3-[(methyl)(3,4-dimethoxyphenethyl)amino]propyl}-4H-1,3-benzoxazin-4-one pamoate 2,3-Dihydro-6,7-dimethoxy-3-{3-[(methyl)(3,4-dimethoxyphenethyl)amino]propyl}-4H-1,3-benzoxazin-4-one pyroglutamate 2,3-Dihydro-6,7-dimethoxy-3-{4-[(methyl)(3,4-dimethoxyphenethyl)amino]butyl}-4H-1,3-benzoxazin-4-one hydrochloride 2,3-Dihydro-6,7-dimethoxy-3-{2-[(methyl)(3,4-dimethoxyphenethyl)amino]ethyl}-4H-1,3-benzoxazin-4-one hydrochloride 2,3-Dihydro-6,7-dimethoxy-3-{3-[(methyl)(3,4-dimethoxybenzyl)amino]propyl}-4H-1,3-benzoxazin-4-one hydrochloride 2,3-Dihydro-6,7-dimethoxy-3-{3-[(4-methoxyphenyl)(benzyl)amino]propyl}-4H-1,3-benzoxazin-4-one hydrochloride 2,3-Dihydro-6,7-dimethoxy-3-{3-[(isopropyl)(3,4-dimethoxyphenethyl)amino]propyl}-4H-1,3-benzoxazin-4-one hydrochloride 2,3-Dihydro-6,7-dimethoxy-3-{3-[(allyl)(3,4-dimethoxyphenethyl)amino]propyl}-4H-1,3-benzoxazin-4-one hydrochloride 2,3-Dihydro-6,7-dimethoxy-3-{3-[(methyl)(4-methoxyphenethyl)amino]propyl}-4H-1,3-benzoxazin-4-one hydrochloride 2,3-Dihydro-6,7-dimethoxy-3-{3-[(methyl)(3-methoxyphenethyl)amino]propyl}-4H-1,3-benzoxazin-4-one hydrochloride 2,3-Dihydro-6,7-dimethoxy-3-{3-[(methyl)(4-chlorophenethyl)amino]propyl}-4H-1,3-benzoxazin-4-one hydrochloride 2,3-Dihydro-6,7-dimethoxy-3-{3-[(methyl)(2-chlorophenethyl)amino]propyl}-4H-1,3-benzoxazin-4-one hydrochloride 2,3-Dihydro-6,7-dimethoxy-3-[3-(3,4-dimethoxyphenethylamino)propyl]-4H-1,3-benzoxazin-4-one hydrochloride 2,3-Dihydro-6,7-dimethoxy-3-[3-(3,4-dimethoxyphenethylamino)ethyl]-4H-1,3-benzoxazin-4-one 2,3-Dihydro-6,7-dimethoxy-3-{3-[(benzyl)(3,4-dimethoxyphenethyl)amino]propyl}-4H-1,3-benzoxazin-4-one hydrochloride 2,3-Dihydro-6,7-dimethoxy-3-{3-[(methyl)(3-phenylpropyl)amino]propyl}-4H-1,3-benzoxazin-4-one hydrochloride 2,3-Dihydro-6,7-dimethoxy-3-{3-[(methyl)(3-phenylpropyl)amino]propyl}-4H-1,3-benzoxazin-4-one hydrochloride 2,3-Dihydro-6,7-dimethoxy-3-{3-[(methyl)(phenethyl)amino]propyl}-4H-1,3-benzoxazin-4-one hydrochloride 2,3-Dihydro-6,7-dimethoxy-2-methyl-3-{3-[(methyl)(3,4-dimethoxyphenethyl)amino]propyl}-4H-1,3-benzoxazin-4-one hydrochloride 2,3-Dihydro-6,7-dimethoxy-2-n-heptyl-3-{3-[(methyl)(3,4-dimethoxyphenethyl)amino]propyl}-4H-1,3-benzoxazin-4-one hydrochloride 2,3-Dihydro-6,7-dimethoxy-2-n-undecyl-3-{3-[(methyl)(3,4-dimethoxyphenethyl)amino]propyl}-4H-1,3-benzoxazin-4-one hydrochloride 2,3-Dihydro-6,7-dimethoxy-2,2-diethyl-3-{3-[(methyl)(3,4-dimethoxyphenethyl)amino]propyl}-4H-1,3-benzoxazin-4-one hydrochloride 2,3-Dihydro-6,7-dimethoxy-2-cyclohexyl-3-{3-[(methyl)(3,4-dimethoxyphenethyl)amino]propyl}-4H-1,3-benzoxazin-4-one hydrochloride 2,3-Dihydro-6,7-dimethoxy-3-{3-[(methyl)(3,4-dimethoxyphenethyl)amino]propyl}-4H-1,3-benzoxazin-4-one-2-spirocyclohexane hydrochloride 2,3-Dihydro-3-{3-[(methyl)(phenethyl)amino]propyl}-2-n-undecyl-4H-1,3-benzoxazin-4-one hydrochloride 2,3-Dihydro-3-{3-[(methyl)(3-methoxyphenethyl)amino]propyl}-6-methoxy-2-undecyl-4H-1,3-benzoxazin-4-one hydrochloride 2,3-Dihydro-7-chloro-3-{3-[(methyl)(3,4-dimethoxyphenethyl)amino]propyl}-4H-1,3-benzoxazin-4-one hydrochloride 2,3-Dihydro-6-chloro-3-{3-[(methyl)(3,4-dimethoxyphenethyl)amino]propyl}-4H-1,3-benzoxazin-4-one hydrochloride 2,3-Dihydro-6-bromo-3-{3-[(methyl)(3,4-dimethoxyphenethyl)amino]propyl}-4H-1,3-benzoxazin-4-one hydrochloride 2,3-Dihydro-6-methyl-3-{3-[(methyl)(3,4-dimethoxyphenethyl)amino]propyl}-4H-1,3-benzoxazin-4-one hydrochloride 2,3-Dihydro-7-methyl-3-{3-[(methyl)(3,4-dimethoxyphenethyl)amino]propyl}-4H-1,3-benzoxazin-4-one hydrochloride 2,3-Dihydro-8-methyl-3-{3-[(methyl)(3,4-dimethoxyphenethyl)amino]propyl}-4H-1,3-benzoxazin-4-one hydrochloride 2,3-Dihydro-6-methoxy-3-{3-[(methyl)(3,4-dimethoxyphenethyl)amino]propyl}-4H-1,3-benzoxazin-4-one hydrochloride 2,3-Dihydro-7-methoxy-3-{3-[(methyl)(3,4-dimethoxyphenethyl)amino]propyl}-4H-1,3-benzoxazin-4-one hydrochloride 2,3-Dihydro-8-methoxy-3-{3-[(methyl)(3,4-dimethoxyphenethyl)amino]propyl}-4H-1,3-benzoxazin-4-one hydrochloride 2,3-Dihydro-8-methoxy-2-methyl-3-{3-[(methyl)(3,4-dimethoxyphenethyl)amino]propyl}-4H-1,3-benzoxazin-4-one hydrochloride 2,3-Dihydro-6-nitro-3-{3-[(methyl)(3,4-dimethoxyphenethyl)amino]propyl}-4H-1,3-benzoxazin-4-one hydrochloride 2,3-Dihydro-6-amino-3-{3-[(methyl)(3,4-dimethoxyphenethyl)amino]propyl}-4H-1,3-benzoxazin-4-one hydrochloride 2,3-Dihydro-6-acetamido-3-{3-[(methyl)(3,4-dimethoxyphenethyl)amino]propyl}-4H-1,3-benzoxazin-4-one hydrochloride 2,3-Dihydro-6-dimethylamino-3-{3-[(methyl)(3,4-dimethoxyphenethyl)amino]propyl}-4H-1,3-benzoxazin-4-one hydrochloride 2,3-Dihydro-5,7-dimethoxy-3-{3-[(methyl)(3,4-dimethoxyphenethyl)amino]propyl}-4H-1,3-benzoxazin-4-one hydrochloride 2,3-Dihydro-6,7-methylenedioxy-3-{[(methyl)(3,4-dimethoxyphenethyl)amino]propyl}-4H-1,3-benzoxazin-4-one hydrochloride 2,3-Dihydro-3-{3-[(methyl)(3,4-dimethoxyphenethyl)amino]propyl}-4H-naphth[2,3-e][1,3]oxazin-4-one hydrochloride 2,3-Dihydro-6,7-dimethoxy-3-[3-(3,4-dimethoxybenzylamino)propyl]-4H-1,3-benzoxazin-4-one hydrochloride 2,3-Dihydro-6,7-dimethoxy-3-[3-{(methyl)[4-(3,4-dimethoxyphenyl)butyl]amino}propyl]-4H-1,3-benzoxazin-4-one hydrochloride 2,3-Dihydro-6,7-dimethoxy-3-[4-(3,4-dimethoxyphenethylamino)butyl]-4H-1,3-benzoxazin-4-one hydrochloride 2,3-Dihydro-6,7-dimethoxy-3-[3-(4-phenylbutylamino)propyl]-4H-1,3-benzoxazin-4-one hydrochloride 2,3-Dihydro-3-[3-(phenethylamino)propyl]-4H-1,3-benzoxazin-4-one hydrochloride 2,3-Dihydro-6-chloro-3-[3-(3,4-dimethoxyphenethylamino)propyl]-4H-1,3-benzoxazin-4-one hydrochloride 2,3-Dihydro-6-chloro-3-{3-[(methyl)(3,4-dimethoxyphenethyl)amino]propyl}-2-methyl-4H-1,3-benzoxazin-4-one hydrochloride 2,3-Dihydro-6-chloro-3-[3-(3,4-dimethoxyphenethylamino)propyl]-2-methyl-4H-1,3-benzoxazin-4-one hydrochloride 2,3-Dihydro-6-chloro-3-[3-(3,4-dimethoxyphenethylamino)propyl]-2-n-heptyl-4H-1,3-benzoxazin-4-one hydrogen oxalate 2,3-Dihydro-6-chloro-3-{3-[(methyl)(3,4-dimethoxyphenethyl)amino]propyl}-2-n-heptyl-4H-1,3-benzoxazin-4-one hydrogen oxalate 2,3-Dihydro-6,8-dichloro-3-[3-(3,4-dimethoxyphenethylamino)propyl]-4H-1,3-benzoxazin-4-one hydrochloride 2,3-Dihydro-6,8-dichloro-3-{3-[(methyl)(3,4-dimethoxyphenethyl)amino]propyl}-4H-1,3-benzoxazin-4-one hydrochloride 2,3-Dihydro-3-[3-(3,4-dimethoxyphenethylamino)propyl]-6-nitro-4H-1,3-benzoxazin-4-one hydrochloride.

3. Pharmaceutical compositions which contain at least one compound as claimed in one of claims 1 or 2, in combination with an inert pharmaceutical vehicle.

4. A compound as claimed in claim 1 wherein $R_1$, $R_2$, $R_3$ and $R_4$ are separately selected from the group consisting of H, Me, Et, i-Pr, MeO, EtO, Br, Cl, F, $NO_2$, $NH_2$, $CH_3$CONH and $Me_2$N radicals.

5. A compound as claimed in claim 1 wherein $R_5$ and $R_6$ are separately selected from the group consisting of H, Me, Et, i-Pr, n-heptyl, n-undecyl, n-pentadecyl, allyl, and cyclohexyl radicals.

6. A compound as claimed in claim 1 wherein $R_7$ is selected from the group consisting of H, Me, Et, i-Pr, n-hexyl, allyl, cyclohexyl, benzyl and phenethyl radicals.

7. A method of treating a patient suffering from a disorder of the cardiovascular system of the group consisting of rapid heart beat, arrhythmia, angina and ischemia which comprises administering to said patient a pharmacologically effective amount of at least one compound as claimed in claim 1 or 2.

* * * * *

UNITED STATES PATENT AND TRADEMARK OFFICE
CERTIFICATE OF CORRECTION

PATENT NO. :   5,071,850
DATED       :   December 10, 1991
INVENTOR(S) :   Jean-Pierre Rieu It is certified that error appears in the above-identified patent and that said Letters Patent is hereby corrected as shown below:

Column 5, line 14     "cylalmide" should be --cylamide--.

Columns 13 and 14     Two formulas are overlapped to look like one formula but should be two separate formulas as follows:

Column 13, lines 1-10

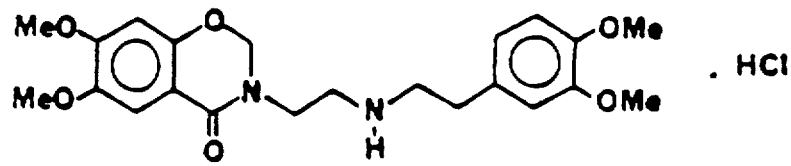

Column 14, lines 5-12

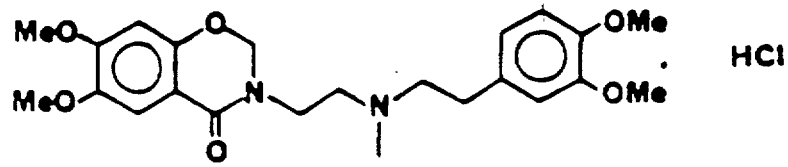

UNITED STATES PATENT AND TRADEMARK OFFICE
CERTIFICATE OF CORRECTION

PATENT NO. : 5,071,850
DATED : December 10, 1991
INVENTOR(S) : Jean-Pierre Rieu

It is certified that error appears in the above-identified patent and that said Letters Patent is hereby corrected as shown below:

| | |
|---|---|
| Column 17, line 6 | In Table III, in the "QTS" column "+12" should be --+10--. |
| Column 18, lines 60-64 | Delete lines 60-64 since it is duplication of lines 53-58. |
| Column 20, line 29 | After "4-one" insert --hydrochloride--. |

Signed and Sealed this

Twentieth Day of July, 1993

Attest:

MICHAEL K. KIRK

*Attesting Officer*     *Acting Commissioner of Patents and Trademarks*